(12) United States Patent
Santiago Flores et al.

(10) Patent No.: US 10,049,448 B2
(45) Date of Patent: Aug. 14, 2018

(54) ARTICULATED STRUCTURE REGISTRATION IN MAGNETIC RESONANCE IMAGES OF THE BRAIN

(71) Applicant: KONINKLIJKE PHILIPS N.V., Eindhoven (NL)

(72) Inventors: Gerardo Santiago Flores, Eindhoven (NL); Octavian Soldea, Eindhoven (NL); Radu Serban Jasinschi, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 53 days.

(21) Appl. No.: 15/109,469

(22) PCT Filed: Jan. 6, 2015

(86) PCT No.: PCT/IB2015/050083
§ 371 (c)(1),
(2) Date: Jul. 1, 2016

(87) PCT Pub. No.: WO2015/101961
PCT Pub. Date: Jul. 9, 2015

(65) Prior Publication Data
US 2016/0328847 A1    Nov. 10, 2016

Related U.S. Application Data

(60) Provisional application No. 61/923,821, filed on Jan. 6, 2014.

(51) Int. Cl.
*G06K 9/00*    (2006.01)
*G06T 7/00*    (2017.01)
(Continued)

(52) U.S. Cl.
CPC .......... *G06T 7/0012* (2013.01); *A61B 5/0042* (2013.01); *A61B 5/055* (2013.01);
(Continued)

(58) Field of Classification Search
None
See application file for complete search history.

(56) References Cited

U.S. PATENT DOCUMENTS 5,633,951 A    5/1997  Moshfeghi
7,792,343 B2   9/2010  Pekar
(Continued)

OTHER PUBLICATIONS

Besl, P, and McKay, H. A method for registration of 3-D shapes, IEEE TPami, 14(2), 239-256, 1992.
(Continued)

*Primary Examiner* — Idowu O Osifade

(57) ABSTRACT

A registration processor (74) is configured to obtain articulated brain substructures using acquired brain image data and template brain image data. The registration processor (74) annotates the brain image data; registers the brain image data with template image data using global brain registration; and registers at least one brain structure of the brain image data a corresponding brain structure of the template image data using a local brain substructure registration. The registration processor (74) articulates articulated substructures of the registered brain structures to improve registration using articulated substructure registration.

11 Claims, 5 Drawing Sheets

(51) Int. Cl.
*A61B 5/00* (2006.01)
*A61B 5/055* (2006.01)
*G06K 9/62* (2006.01)
*G06T 3/60* (2006.01)
*G06T 7/33* (2017.01)
*G06T 7/37* (2017.01)

(52) U.S. Cl.
CPC .......... *A61B 5/4064* (2013.01); *G06K 9/6215* (2013.01); *G06K 9/6248* (2013.01); *G06T 3/60* (2013.01); *G06T 7/33* (2017.01); *G06T 7/37* (2017.01); *A61B 2576/026* (2013.01); *G06T 2207/10088* (2013.01); *G06T 2207/20016* (2013.01); *G06T 2207/30016* (2013.01)

(56) References Cited

U.S. PATENT DOCUMENTS

| | | | |
|---|---|---|---|
| 2007/0276219 A1* | 11/2007 | K.N. ................ | G06T 7/60 600/410 |
| 2008/0205719 A1 | 8/2008 | Pekar et al. | |
| 2008/0292194 A1* | 11/2008 | Schmidt ............. | G06T 7/0012 382/217 |
| 2009/0220171 A1 | 9/2009 | Liu et al. | |
| 2011/0216954 A1 | 9/2011 | Sundar | |
| 2013/0039550 A1 | 2/2013 | Blum | |
| 2013/0304710 A1* | 11/2013 | Nachev ............. | G06K 9/6284 707/690 |
| 2014/0037171 A1* | 2/2014 | Bhat .................. | G06T 11/003 382/131 |

OTHER PUBLICATIONS

Viola, P. and Wells III, W. M. Alignment by Maximization of Mutual Information, International Journal of Computer Vision, 24(2), 137-154, 1997.

Miller, M. I., Christensen, G. E., Amit, Y., and Grenander, U., Mathematical Textbook of Deformable Neuroanatomies, Proc Natl Acad Sci., 15, 11944-11948, 1993.

Grenander, U., and Miller, M. I., Computational anatomy: an emerging discipline, Quarterly of Applied Mathematics—Special issue on current and future challenges in the applications of mathematics, vol. LVI Issue 4, Dec. 1998, American Mathematical Society Boston, MA, USA.

Klein, A, et al., Evaluation of 14 nonlinear deformation algorithms applied to human brain MRI registration, Neuroimage, 46(3):786-802, 2009.

Elastix: http://elastix.isi.uu.nl/ downloaded Jun. 27, 2016.

ITK: www.itk.org downloaded Jun. 27, 2016.

VTK: www.VTK.org.

Chui H et al: "Registration of Cortical Anatomical Structures Via Robust 3D Point Matching", Information Processing in Medical Imaging. InternationalConference. Proceedings, XX, XX Jun. 28, 1999 (Jun. 28, 1999), pp. 168-181.

Pitiot A et al: "Piecewise affine registration of biological images for volume reconstruction",Medical Image Analysis, Oxford University Press, Oxofrd, GB,vol. 10, No. 3, Jun. 1, 2006 (Jun. 1, 2006),pp. 465-483.

Commowick 0 et al: "An efficient locally affine framework for the smooth registration of anatomical structures". Medical Image Analysis, Oxford University Press, Oxofrd, GB,vol. 12, No. 4, Aug. 1, 2008 (Aug. 1, 2008),pp. 427-441.

Gerardo Santiago Flores et al: "Automatic Segmentation of Hippocampal Substructures", Jul. 2, 2012 (Jul. 2, 2012), XP055185638,Retrieved from the Internet:URL:http://alexandria.tue.nl/extral/afstve rsl/wsk-i/flores2012.pdf [retrieved on Apr. 24, 2015].

* cited by examiner

ARTICULATED STRUCTURE REGISTRATION IN MAGNETIC RESONANCE IMAGES OF THE BRAIN

CROSS REFERENCE TO RELATED APPLICATIONS

This application is a U.S. national phase application of International Application No. PCT/IB2015/050083, filed on Jan. 6, 2015, which claims the benefit of U.S. provisional Application Ser. No. 61/923,821 filed on Jan. 6, 2014 and is incorporated herein by reference.

Alzheimer's disease and other types of dementia are debilitating conditions affecting millions. Early detection of the onset of such conditions can facilitate early intervention and improve patient health, quality of life, and overall outcome. The conditions have been linked to shrinkage of the hippocampus part of the brain.

The registration of brain magnetic resonance (MR) volumes is a fundamental operation for the processing of brain information. This information is used in the diagnosis of brain tumors, children's brain development, stroke treatments, and neurodegenerative diseases. The registration of one brain—target brain to be processed for diagnosis—to another brain—template or atlas brain that contains known information about its structures—allows clinicians to compare voxel-wise shape and intensity information between the target and template brains. The identification and quantification of shape/intensity differences between the target and template brains allows clinicians to, automatically or semi-automatically, generate features for brain diagnosis.

Current methods for brain registration are divided into: (i) global and (ii) local registration. In the global registration method the whole target brain is registered to the template brain by a combination of translation—of the center of mass—and rotation, such as, by an affine transformation. In the local registration, each voxel in the target brain is transformed to match the shape and intensity characteristics of template brain voxels.

These currently known methods, presented above, propose the registration of 2-D/3-D regions/objects by either global registration, such as, affine registration, or local registration, in computational anatomy, or a combination of both. However, these registration methods do not incorporate object structure information, dealing either with global or local registration.

In accordance with one embodiment, a brain registration system, comprising: a registration processor having a processor configured to: annotate brain image data; register the brain image data with template image data using global brain registration; register at least one brain structure of the brain image data to a corresponding brain structure of the template image data using a local brain sub-structure registration; and articulate articulated sub-structures of the registered brain structures to improve registration using articulated sub-structure registration.

In accordance with one method, a method for brain registration, comprising: annotating brain image data; registering the brain image data with template image data using global brain registration; registering at least one brain structure of the brain image data a corresponding brain structure of the template image data using a local brain sub-structure registration; and articulating articulated sub-structures of the registered brain structures to improve registration using articulated sub-structure registration.

In accordance with another embodiment, a brain registration system, comprising: an annotation module to annotate brain image data; a global registration module to register the brain image data with template image data using global brain registration; a local registration module to register at least one brain structure of the brain image data a corresponding brain structure of the template image data using a local brain sub-structure registration; and an articulation module to articulate articulated sub-structures of the registered brain structures to improve registration using articulated sub-structure registration.

One advantage is increased overlap between a brain MRI and a template brain.

Another advantage is a bridge between global and local brain registration methods.

Still further advantages of the present invention will be appreciated to those of ordinary skill in the art upon reading and understand the following detailed description.

The present application provides a method that works between the global and the local registrations. The present application provides for registration of brain structures which are represented by a set of articulated sub-structures. This takes into account that anatomically and functionally brain structures, such as the hippocampus, thalamus, and the putamen are made of a set of sub-structures. The shape, pose, and intensity of these sub-structures vary from brain to brain and even between different hemispheres of the same brain. Each brain sub-structure is described by a rigid shape and its associated surface intensity values and it is deformed as an articulated object. This articulated deformation describes a set of rotations about the points of contacts that are similar to mechanical hinges. Each sub-structure can also be broken up in smaller sub-parts in order to make the registration as precise as possible.

Figure 1:
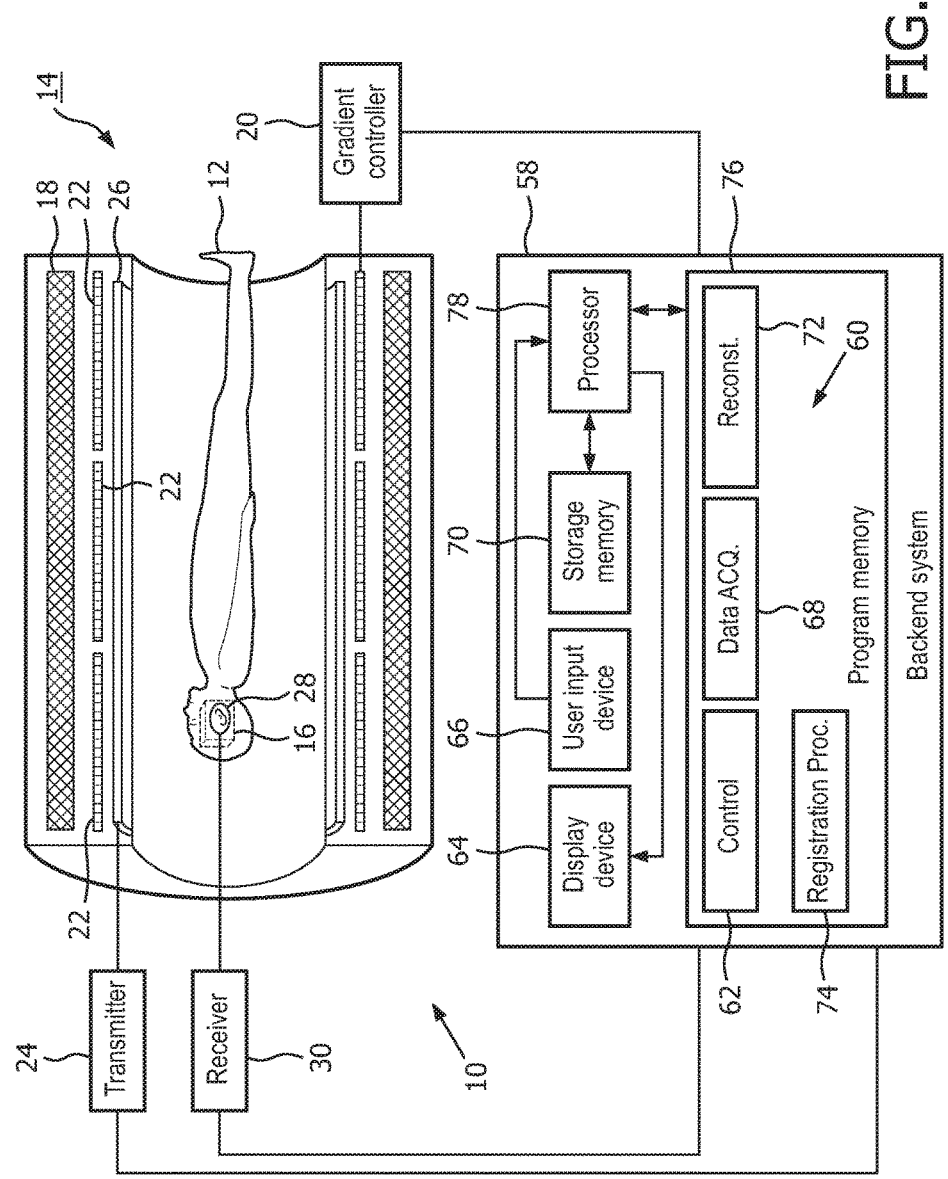
FIG. 1 depicts an MRI system for articulated structure registration in magnetic resonance images of the brain.

With reference to FIG. 1, a magnetic resonance (MR) imaging system 10 utilizes MR to image a region of interest (ROI), i.e. brain, of a patient 12. The system 10 includes a scanner 14 defining an imaging volume 16 (indicated in phantom) sized to accommodate the ROI. A patient support can be employed to support the patient 12 in the scanner 14 and facilitates positioning the ROI in the imaging volume 16.

The scanner 14 includes a main magnet 18 that creates a strong, static $B_0$ magnetic field extending through the imaging volume 16. The main magnet 18 typically employs superconducting coils to create the static $B_0$ magnetic field. However, the main magnet 18 can also employ permanent or resistive magnets. Insofar as superconducting coils are employed, the main magnet 18 includes a cooling system, such as a liquid helium cooled cryostat, for the superconducting coils. The strength of the static $B_0$ magnetic field is commonly one of 0.23 Tesla, 0.5 Tesla, 1.5 Tesla, 3 Tesla, 7 Tesla, and so on in the imaging volume 16, but other strengths are contemplated.

A gradient controller 20 of the scanner 14 is controlled to superimpose magnetic field gradients, such as x, y and z gradients, on the static $B_0$ magnetic field in the imaging volume 16 using a plurality of magnetic field gradient coils 22 of the scanner 14. The magnetic field gradients spatially encode magnetic spins within the imaging volume 16. Typically, the plurality of magnetic field gradient coils 22 include three separate magnetic field gradient coils spatially encoding in three orthogonal spatial directions.

Further, one or more transmitters 24, such as a transceiver, are controlled to transmit $B_1$ resonance excitation and manipulation radiofrequency (RF) pulses into the imaging volume 16 with one or more transmit coil arrays, such as a whole body coil 26 and/or a surface coil 28, of the scanner 14. The $B_1$ pulses are typically of short duration and, when taken together with the magnetic field gradients, achieve a selected manipulation of magnetic resonance. For example, the $B_1$ pulses excite the hydrogen dipoles to resonance and the magnetic field gradients encode spatial information in the frequency and phase of the resonance signal. By adjusting the RF frequencies, resonance can be excited in other dipoles, such as phosphorous, which tend to concentrate in known tissues, such as bones.

One or more receivers 30, such as a transceiver, are controlled to receive spatially encoded magnetic resonance signals from the imaging volume 16 and demodulate the received spatially encoded magnetic resonance signals to MR data sets. The MR data sets include, for example, k-space data trajectories. To receive the spatially encoded magnetic resonance signals, the receivers 30 use one or more receive coil arrays, such as the whole body coil 26 and/or the surface coil 28, of the scanner 14. The receivers 30 typically store the MR data sets in a buffer memory.

A backend system 58 of the system 10 images the ROI using the scanner 14. The backend system 58 is typically remote from the scanner 14 and includes a plurality of modules 60, discussed hereafter, to perform the imaging of the ROI using the scanner 14. Advantageously, the backend system can characterize myocardium without the influence of imprecise inversion time selection and provide true quantitative signal quantification on a standardized scale.

A control module 62 of the backend system 58 controls overall operation of the backend system 58. The control module 62 suitably displays a graphical user interface (GUI) to a user of the backend system 58 using a display device 64 of the backend system 58. Further, the control module 62 suitably allows the operator to interact with the GUI using a user input device 66 of the backend system 58. For example, the user can interact with the GUI to instruct the backend system 58 to coordinate the imaging of the ROI.

A data acquisition module 68 of the backend system 58 performs MR scans of the ROI. For each MR scan, the data acquisition module 68 controls the transmitters 24 and/or the gradient controller 20 according to scan parameters, such as number of slices, to implement an imaging sequence within the imaging volume 16. An imaging sequence defines a sequence of $B_1$ pulses and/or magnetic field gradients that produce spatially encoded MR signals from the imaging volume 16. Further, the data acquisition module 68 controls the receivers 30, and the tune/detune control signal of the driver circuit 36, according to scan parameters to acquire spatially encoded MR signals to an MR data set. The MR data set is typically stored in at least one storage memory 70 of the backend system 58.

In preparing for MR acquisition, the ROI is positioned within the imaging volume 16. For example, the patient 12 is positioned on the patient support. The surface coil 28, e.g.

a 8 or 32 channel receive head coil, is then positioned on the patient 12 and the patient support moves the ROI into the imaging volume 16.

A reconstruction module 72 of the backend system 58 reconstructs the MR data sets of the MR diagnostic scans into MR images or maps of the ROI. This includes, for each MR signal captured by the MR data sets, spatially decoding the spatial encoding by the magnetic field gradients to ascertain a property of the MR signal from each spatial region, such as each pixel or voxel. The intensity or magnitude of the MR signal is commonly ascertained, but other properties related to phase, relaxation time, magnetization transfer, and the like can also be ascertained. The acquired MR images or maps can be typically stored in the storage memory 70. The memory 70 also stores brain templates or atlases which depict normal and/or various disease conditions.

Figure 2:
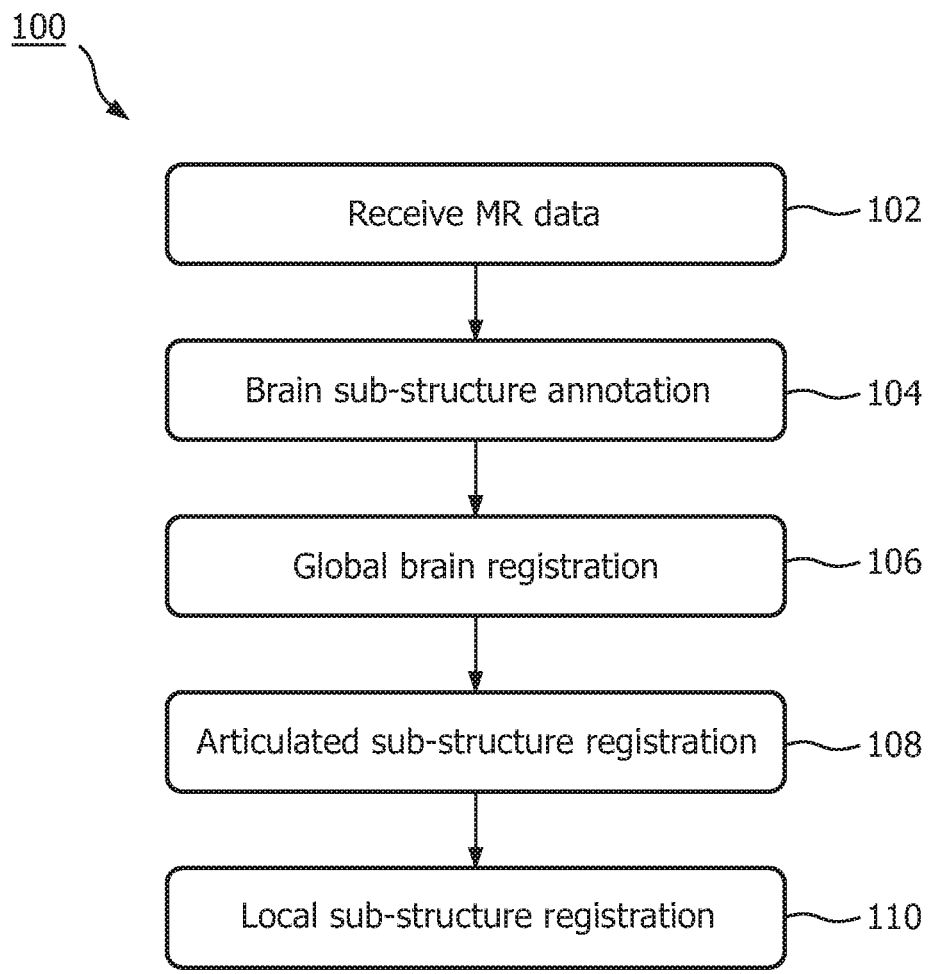
FIG. 2 depicts a method for articulated structure registration in magnetic resonance images of the brain.

A registration processor 74 of the backend system 58 carries out an enhanced method 100 of articulated structure registration within a target brain, shown in FIG. 2. The method 100 allows improved registration of segmented structures within the target brain to template brain structures. The method 100 describes the segmentation and registration of with hippocampus sub-structures, but other anatomical structures are also contemplated.

Figure 3:
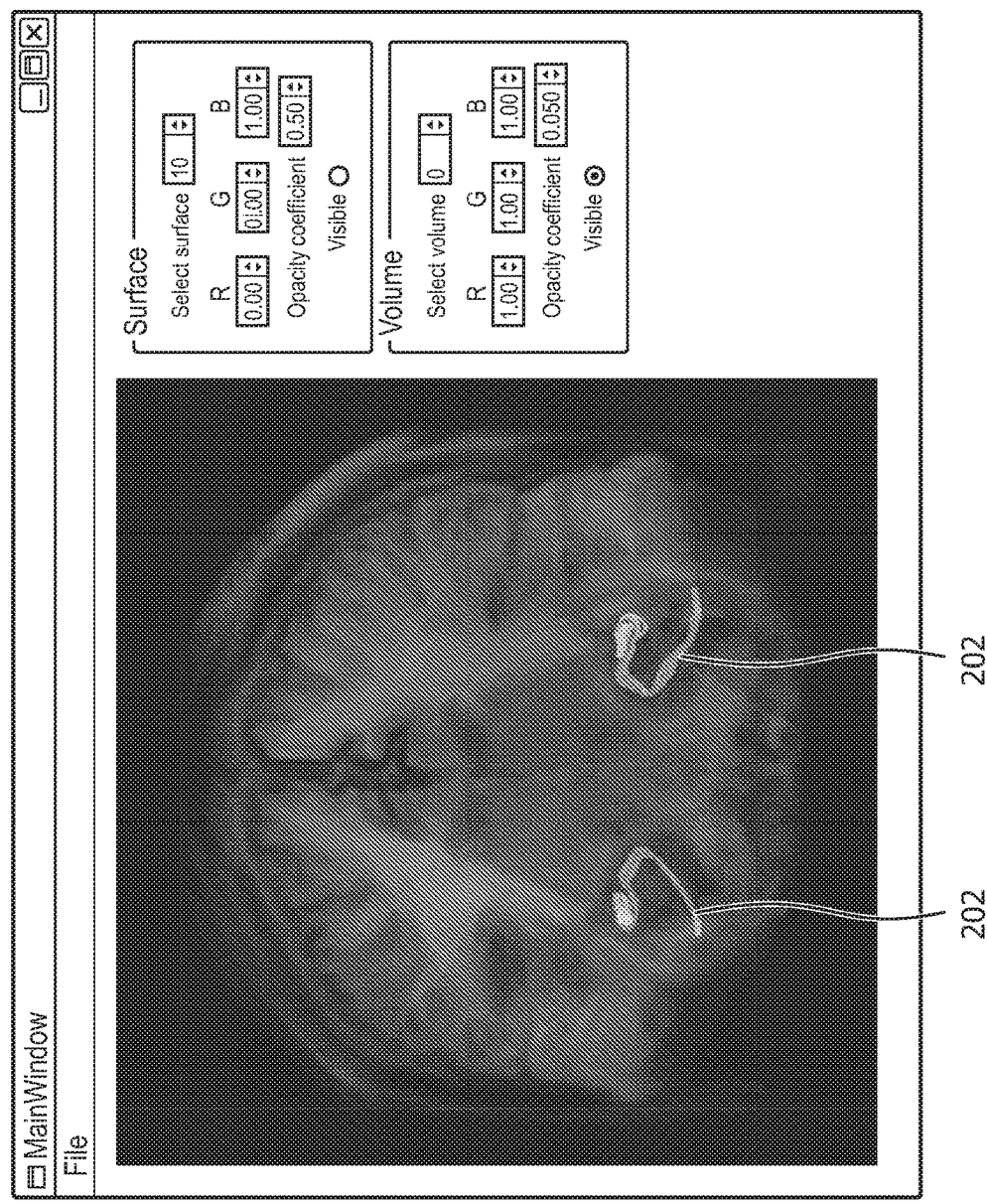
FIG. 3 depicts an annotated brain sub-structure superimposed on brain tissue.

According to the illustrated method 100, the registration processor 74 receives MR data from the data acquisition module 68. The MR data includes MR images taken of the target brain or other region of interest. The registration processor 74 then performs brain sub-structure annotation 104, e.g. segmentation of brain structures of internal and adjacent structures in the imaging region. The segmented structures are identified, e.g. based on location shape, neighboring structures, and the like, and labeled. The brain sub-structure annotation 104 determines an a priori brain sub-structure shape and pose based on expert annotation. With reference to FIG. 3, expertly annotated hippocampus sub-structures 202 are superimposed on an acquired target brain image.

The registration processor 74 preforms global brain registration 106. The registration processor 74 first computes the centre of mass (CM) of the acquired target and reference template MRI brain images based on zero and first order moments. Based on this information the template brain image is translated so that its CM is co-located with the CM of the acquired target brain image. Second, the registration processor 74 computes a three orthogonal axis of orientation for the template and acquired target brain images based on moments, and then rotates the template brain coordinate axes such that it aligns with that of the acquired target brain image's coordinate axes. Third, the registration processor 74 scales the template brain volume of interest along the three coordinate axes so that it maximizes the overlap of the two brain volumes; this is called isotropic moments-based global registration. In one embodiment, scaling is not performed which is called anisotropic moments-based global registration. In one embodiment, global brain registration is performed using registration software such as Elastix.

To find a volume of interest, i.e. the entire hippocampus, the registration processor 74 computes the intersection of boundaries in each orthogonal direction of the template brain. The registration processor 74 uses the template volume of interest to compute the volume of interest of the target brain.

Figure 4:
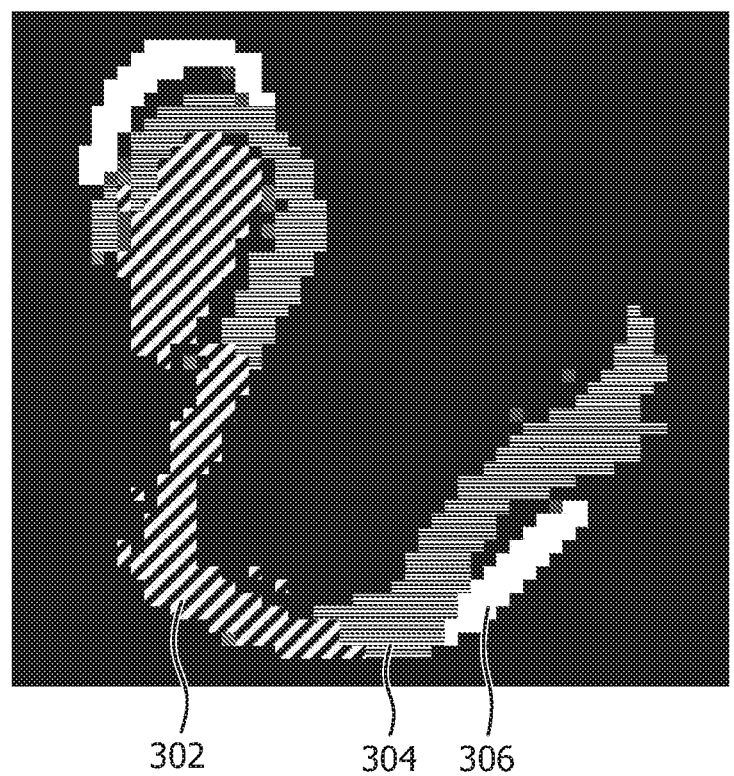
FIG. 4 depicts a hippocampus target registered to a template structure.
Figure 5:
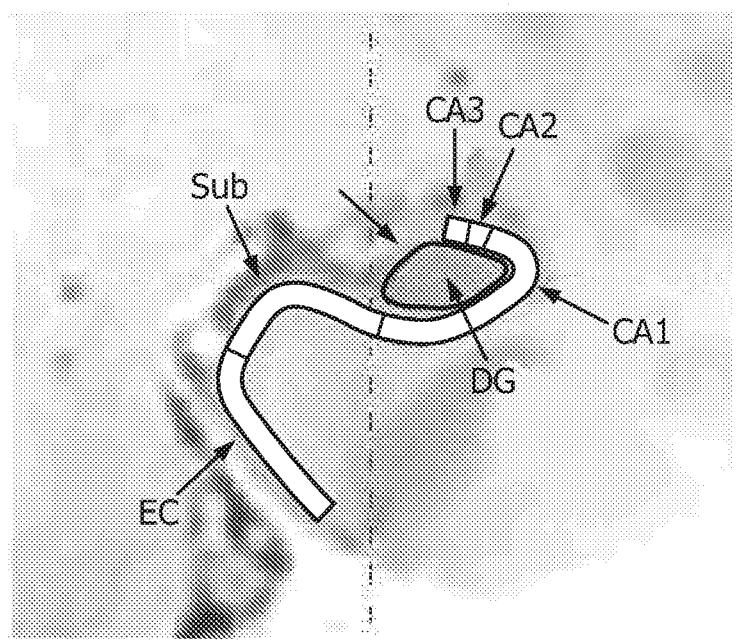
FIG. 5 depicts a detailed method for articulated sub-structure registration.

The registration processor 74 performs articulated sub-structure registration 108. The articulated sub-structure registration uses the existence of articulations inside brain structures to align one articulatable image, e.g. the acquired target brain MM, to a fixed one, e.g. the template brain image. With reference to FIG. 4, a registered target hippocampus is overlaid with template brain images, parts of the hippocampus are superimposed and parts are misaligned. Where the hippocampus of the acquired target brain image is registered to the template brain image correctly 302 the image is color coded, e.g. green (diagonal stripe region). Where the hippocampus parts are incorrectly 304 aligned, the target image is color coded, e.g. in red (horizontal striped region), and the misaligned portion of the hippocampus structure 306 in the reference template image is color coded in a third color, e.g. white (white). Articulated sub-structure registration 108 compensates for the incorrect registration 304 by rotating each of the sub-structures, e.g. misaligned hippocampus parts in the acquired target image, such that overlap onto the target and template images 306 increases. The articulated sub-structure registration 108 articulates sub-structures or portions of the hippocampus relative to other portions of the hippocampus to increase the overlap. With reference to FIG. 5, an articulated hippocampus is shown divided into sub-structures according to parts of the hippocampus. The sub-structures include the subiculum SUB, dentate gyrus DG, enthorinal cortex EC, or cornu ammonis CA1, CA2, CA3.

To find a volume of interest of each sub-structure, the registration processor 74 computes the intersection of boundaries in each orthogonal direction of the template brain. The registration processor 74 uses the template sub-structure volumes of interest to compute the sub-structure volumes of interest of the target brain.

The registration processor 74 performs a local brain registration 110 to register target brain structures to template brain structures. The local registration transforms each voxel in a target brain image to match the shape and intensity characteristics of corresponding template brain image voxels. The local brain registration includes, for example, applying BSplines for local pixel (voxel) intensity interpolation. In one embodiment, local brain registration is performed using registration software such as Elastix or FSL FLIRT.

Figure 6:
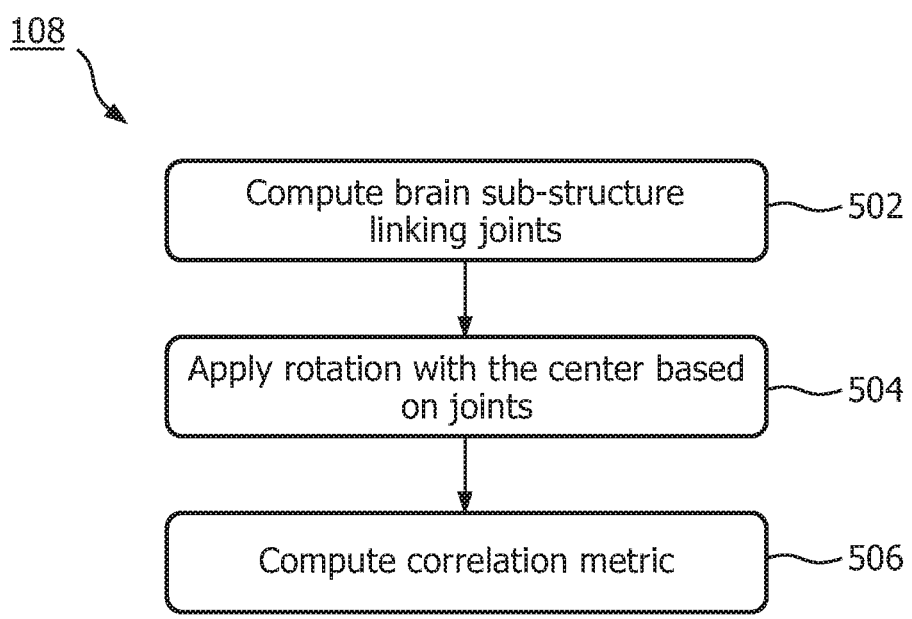
FIG. 6 depicts a diagram of structure rotation about a joint.
Figure 7:
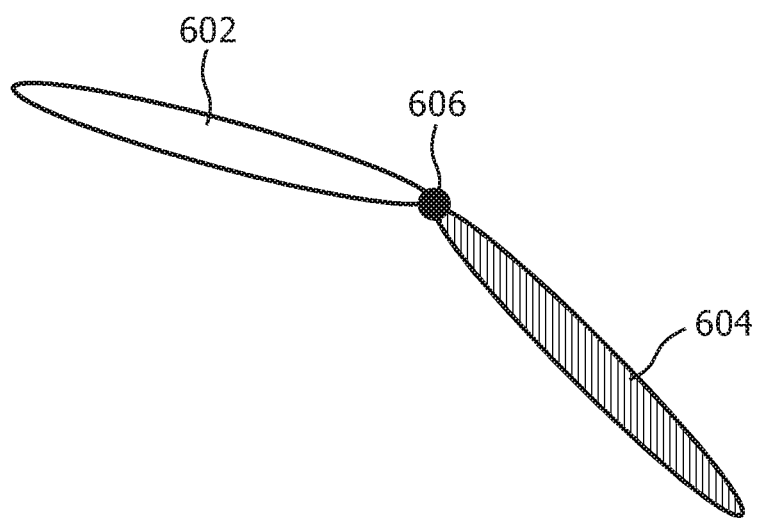
FIG. 7 depicts a joint between two sub-structures.

With reference to FIG. 6, the registration processor 74 performs articulated sub-structure registration 108 by first computing brain sub-structure linking joints 502. Linking joints are linking points by which two sub-structures, e.g. misaligned and aligned hippocampus portions are connected. MR image pixels/voxels are mapped to a physical point in the space such that every pixel contains the intensity value of the image and the physical position of that value. The registration processor 74 represents the joint between two sub-structures as a physical point in the space. With reference to FIG. 7, two objects 602/604 in an image represent two sub-structures, such as hippocampus portions 302 and 304 in FIG. 4. The registration processor 74 finds the joint 606 as the brain sub-structure linking joint. The registration processor 74 calculates the joint 606 by calculating a pair of pixels/voxels (one pixel/voxel from structure 602 and one pixel from structure 604) with minimum Euclidean distance between them. In one embodiment, a set of pairs of pixels is calculated because there might be more than one pair with the same minimum distance. The registration processor 74 calculates the pairs with minimum Euclidian distance by obtaining all combinations of pairs of pixels/voxels and comparing the distance between each pair. The registration processor 74 calculates the average location of each of the pixels/voxels from each structure 602,604 from the calculated set of pairs to find an extreme point of each structure. The registration processor 74 computes the middle point between the extreme points as the joint 606.

The registration processor 74 applies a rotation 504 about the calculated joint 606 to maximize alignment. In the hippocampus example, the registration processor 74 rotates the misaligned portion of the hippocampus in the acquired target brain image about the joint 606 to optimize the alignment with the corresponding hippocampus portion in the template brain image. The registration processor 74 first calculates a similarity metric 506 between the acquired image and the template image to maximize the similarity between the images according to the similarity metric. The similarity metric can be one of sum of square differences, normalized correlation coefficient, or mutual information metrics and the like. Using the similarity metric, the registration processor 74 calculates an optimal transformation e.g. articulating movement. In one embodiment, the registration processor 74 uses an iterative process to calculate the optimal transform in which the registration processor 74 applies a rotation of a preselected amount and computes the similarity metric, then increases the rotation about the joint 606 and re-computes the similarity metric. The registration processor 74 iteratively applies the transform to the MRI binary image which maximizes overlap between the target structure and the MM image.

Each of the plurality of modules 60, 100, 110 can be embodied by processor executable instructions, circuitry (i.e., processor independent), or a combination of the two. The processor executable instructions are stored on at least one program memory 76 of the backend system 58 and executed by one or more processors 78 of the backend system 58. As illustrated, the plurality of modules 60 is embodied by processor executable instructions. However, as is to be appreciated, variations are contemplated. For example, the data acquisition module 68 can be circuitry.

As used herein, a memory includes one or more of: a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; and the like. Further, as used herein, a processor includes one or more of a microprocessor, a microcontroller, a graphic processing unit (GPU), an application-specific integrated circuit (ASIC), an FPGA, and the like; a controller includes: (1) a processor and a memory, the processor executing computer executable instructions on the memory embodying the functionality of the controller; or (2) analog and/or digital hardware carrying out the functionality of the controller; a user input device includes one or more of a mouse, a keyboard, a touch screen display, a button, a switch, a voice recognition engine, and the like; a database includes one or more memories; a user output device includes a display device, a auditory device, and the like; and a display device includes one or more of a liquid crystal display (LCD) display, a light emitting diode (LED) display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A brain registration system, comprising:
a main magnet configured to create a strong, static magnetic field through an imaging volume;
magnetic field gradient coils configured to generate magnetic field gradients in the imaging volume;
one or more RF coils configured to transmit radio frequency pulses into the imaging volume and receive magnetic resonance echo signals from the imaging volume;
a transmitter configured to control the one or more RF coils to transmit magnetic resonance excitation and manipulation pulses into the imaging volume;
one more receivers configured to demodulate the magnetic resonance echo signals from the one or more RF coils;
a back end system including a memory configured to store brain templates, a user input device, a display device, and one or more processors configured to:
reconstruct the demodulated magnetic resonance echo signals from the receiver into a brain image,
segment the brain image to annotate brain image data,
globally register the brain image with a template image retrieved from the storage memory,
identify an articulated structure in the segmented brain image, the articulated structure including a pair of sub-structures connected by a linking joint,
rotate the articulated sub-structures relative to each other about the linking joint to improve registration to maximize image similarity of the articulated structure in the brain image and the brain template, and
control the display device to display the brain image including the articulated structure.

2. The system according to claim 1, wherein the one or more processors are further configured to:
iteratively rotate the at least one of the sub-structures of the articulated structure in the brain image and the brain template about the linking joint,
compute a similarity metric between the brain image articulated structure and the brain template articulated structure for each iteration, and
select one of the iterations that maximizes the similarity metric.

3. The system according to claim 1, wherein the one or more processors are further configured to apply a transform to the brain image to maximize overlap between the articulated structure in the brain image and the brain template.

4. The system according to claim 1, wherein the one or more processors are further configured to identify the linking joint by:
calculating a Euclidian distance for all pairs of pixels/voxels between the sub-structures of the articulated structure;
selecting a pair of pixels/voxels having a minimum Euclidian distance therebetween; and
computing a middle point between the selected pair of pixels/voxels as the linking joint between the sub-structures.

5. The system according to claim 1, wherein the globally registering of the brain image with the brain template includes an isotropic moments-based global registration.

6. A brain registration method, comprising:
with a main magnet, creating a strong, static magnetic field through an imaging volume;
with magnetic field gradient coils, generating magnetic field gradients in the imaging volume;
with one or more RF coils, transmitting radio frequency pulses into the imaging volume and receiving magnetic resonance echo signals from the imaging volume;
with a transmitter, controlling the one or more RF coils to transmit magnetic resonance excitation and manipulation pulses into the imaging volume;
with one more receivers, demodulating the magnetic resonance echo signals from the one or more RF coils;
with one or more processors of a back end system including a memory configured to store brain templates, a user input device, a display device, and the one or more processors:
reconstructing the demodulated magnetic resonance echo signals from the receiver into a brain image,
segmenting the brain image to annotate brain image data,
globally registering the brain image with a template image retrieved from the storage memory,
identifying an articulated structure in the segmented brain image, the articular structure including a pair of sub-structures connected by a linking joint,
rotating the articulated sub-structures relative to each other about the linking joint to improve registration to maximize image similarity of the articulated structure in the brain image and the brain template, and
controlling the display device to display the brain image including the articulated structure.

7. The method according to claim 6, further including with the one or more processors:
iteratively rotating the at least one of the sub-structures of the articulated structure in the brain image and the brain template about the linking joint; and
computing a similarity metric between the brain image articulated structure and the template image articulated structure for each iteration; and
selecting the iteration that maximizes the similarity metric.

8. The method according to claim 6, wherein identifying the linking joint includes with the one or more processors:
calculating a Euclidian distance for all pairs of pixels/voxels between the articulated sub-structures of the articulated structure;
selecting a pair of pixels/voxels having a minimum Euclidian distance from each other; and
computing a middle point between the selected pair of pixels/voxels as the linking joint between the sub-structures.

9. A non-transitory computer readable medium having instructions configured to control the one or more processors to perform the method of claim 6.

10. A brain registration system comprising:
a registration processor having a processor configured to:
annotate brain image data, thereby obtaining a segmentation of brain structures in the brain image data;
register the brain image data with template image data using global brain registration, thereby obtaining registered brain image data comprising registered brain structures;
compensate for incorrect registration of at least one structure of the registered brain structure, which structure includes a pair of sub-structures, said compensation comprising:
identifying a linking joint between a pair of sub-structures of the registered brain structures;
rotating at least one of the pair of sub-structures in the registered brain image data about the linking joint to maximize a similarity to the template image data in accordance with a similarity metric which is computed between the registered brain image data comprising said rotated sub-structure and the template image data.

11. The system according to claim 10, further including:
a reconstruction processor configured to reconstruct brain image data into brain images; and
a display device configured to display the brain images including the articulated structure with the sub-structures rotated to maximize the similarity.

* * * * *